United States Patent [19]

Takano et al.

[11] Patent Number: 5,243,096
[45] Date of Patent: Sep. 7, 1993

[54] OPTICALLY ACTIVE PENTANE DERIVATIVES AND INTERMEDIATES THEREOF, AND PROCESS FOR MANUFACTURING SAME

[75] Inventors: Seiichi Takano; Kunio Ogasawara, both of Sendai, Japan

[73] Assignee: Asahi Denka Kogyo K.K., Tokyo, Japan

[21] Appl. No.: 876,373

[22] Filed: Apr. 30, 1992

Related U.S. Application Data

[62] Division of Ser. No. 714,613, Jun. 13, 1991, Pat. No. 5,136,061.

[30] Foreign Application Priority Data

Jun. 14, 1990 [JP] Japan ................... 2-157816

[51] Int. Cl.$^5$ .................. C07C 29/36; C07C 33/042
[52] U.S. Cl. ................... 568/873; 549/518
[58] Field of Search ............. 568/873, 874; 549/518

[56] References Cited

U.S. PATENT DOCUMENTS

| | | | |
|---|---|---|---|
| 2,016,182 | 1/1938 | Kreimeier | 568/873 |
| 2,525,672 | 10/1950 | Heilbron et al. | 568/873 |
| 2,996,552 | 8/1961 | Blumenthal | 568/874 |
| 3,381,039 | 4/1968 | Marbet | 549/430 |
| 3,442,930 | 5/1969 | McConnell et al. | 568/852 |
| 3,576,889 | 4/1971 | Martin et al. | 568/874 |
| 3,584,010 | 6/1971 | Marbet | 549/430 |
| 3,880,911 | 4/1975 | Saucy | 560/112 |
| 4,045,475 | 8/1977 | Chan et al. | 568/909.5 |
| 4,311,645 | 1/1982 | Rosenberger | 568/873 |
| 4,380,675 | 4/1983 | Gebauer et al. | 568/909.5 |
| 4,855,481 | 8/1989 | Guindon et al. | 549/561 |
| 5,068,368 | 11/1991 | Smith et al. | 568/874 |
| 5,136,061 | 8/1992 | Takano et al. | 549/512 |

FOREIGN PATENT DOCUMENTS

| | | | |
|---|---|---|---|
| 11930 | 1/1982 | Japan | 568/909.5 |
| 32727 | 2/1985 | Japan | 568/852 |
| 1158974 | 7/1986 | Japan | 549/518 |

745888  7/1980  U.S.S.R. .................. 568/873

OTHER PUBLICATIONS

1984–1985 Aldrich Catalog/Handbook of Fine Chemicals, Aldrich Chemical Company, Inc., Milwaukee, Wisconsin, 1984, pp. 594, 596.

*Primary Examiner*—Joseph E. Evans
*Attorney, Agent, or Firm*—Sherman and Shalloway

[57] ABSTRACT

An optically active pentane compound of the general formula (I):

$$D-CH-{}^*CH-CH_2-{}^\#CH-CH_2-R_2 \quad (I)$$
$$\phantom{D-CH-}|\phantom{CH-}|\phantom{CH_2-}|$$
$$\phantom{D-CH-}A\phantom{CH-}B\phantom{CH_2-}R_1$$

wherein $R_1$ represents a lower alkyl group having 1 to 4 carbon atoms, $R_2$ represents a lower alkoxycarbonyl group having an alkoxy moiety of 1 to 4 carbon atoms, or a straight-chain or branched alkyl group having 1 to 7 carbon atoms which is unsubstituted or substituted with a hydroxy or protected hydroxy group, A represents a halogen atom, hydroxy, protected hydroxy, or ethynyl group, or a group of the formula $$-\underset{\underset{CH_3}{|}}{CH}-CH_2OH,$$

B represents a hydrogen atom, hydroxy, protected hydroxy or acyloxy group, D represents a hydrogen atom, or A and B together can form an acetal or epoxy group, A and D together can form an ethylidene group, and B and D together can form a carbon-carbon direct bond, and the chiral central carbon atoms marked with symbols *, # and ∴ in said formula (I) alternatively have one of an R-configuration and an S-configuration Further, intermediates thereof, and a process for manufacturing the above compound are also disclosed

7 Claims, No Drawings

OPTICALLY ACTIVE PENTANE DERIVATIVES AND INTERMEDIATES THEREOF, AND PROCESS FOR MANUFACTURING SAME

This is a division of U.S. application Ser. No. 07/714,613 filed Jun. 13, 1991 now U.S. Pat. No. 5,136,061.

BACKGROUND OF THE INVENTION

1. Field of the Invention

The present invention relates to an optically active novel compound and intermediate products thereof, and a process for the manufacture of same.

2. Description of the Related Art

Vitamin E is a methylated derivative of a tocopherol, and includes eight kinds of naturally occurring compounds, i.e., $\alpha$-, $\beta$-, $\gamma$-, and $\delta$-tocopherols, and $\alpha$-, $\beta$-, $\gamma$-, and $\delta$-tocotrienols. Although tocopherols and tocotrienols include d-form, l-form or dl-form optical isomers, naturally occurring compounds showing optical activities have d-form. Synthesized tocopherols are generally prepared in the form of a diastereomer, and it is known that a chirality of the carbon atom of the 2-position in the chroman ring has a considerable affect on the physiological activities of tocopherols.

A method of synthesizing optically active tocopherols from optically active starting materials is described in, for example, N. Cohen, et al, Journal of the American Chemical Society, 101:22, Oct. 24, 1979, 6710-6716. In the method of Cohen, et al, an optically active desired $\alpha$-tocopherol is obtained by using an optically active benzopyran derivative as a starting material, to form an optically active chroman-2-methanol derivative, and then performing a Wittig coupling of the chroman derivative to form the final $\alpha$-tocopherol while retaining the chirality of the starting material. In this method, however, a resolution process is required to obtain the optically active starting material, and a poisonous hydrocyanic acid must be used during the course of the synthesis process.

SUMMARY OF THE INVENTION

Accordingly, an object of the present invention is to provide intermediates from which naturally occurring or non-occurring tocopherols can be alternatively prepared, without the need for a resolution process and the need to use poisonous reagents, and which can be prepared from an easily available starting material having an optical activity.

Other objects and advantages of the present invention will be apparent from the following description.

In accordance with the present invention, there is provided an optically active pentane compound of the general formula (I):

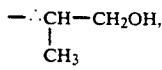

$$D-CH-*CH-CH_2-\#CH-CH_2-R_2 \quad (I)$$
$$\phantom{D-CH-}|\phantom{*CH-CH_2-\#}|\phantom{CH-CH_2-R_2}$$
$$\phantom{D-CH-}A\phantom{*}B\phantom{-CH_2-\#}R_1$$

wherein $R_1$ represents a lower alkyl group having 1 to 4 carbon atoms, $R_2$ represents a lower alkoxycarbonyl group having an alkoxy moiety of 1 to 4 carbon atoms, or a straight-chain or branched alkyl group having 1 to 7 carbon atoms which is unsubstituted or substituted with a hydroxy or protected hydroxy group, A represents a halogen atom, hydroxy, protected hydroxy, or ethynyl group, or a group of the formula $$-CH-CH_2OH,$$
$$\phantom{-}|$$
$$\phantom{-}CH_3$$

B represents a hydrogen atom, hydroxy, protected hydroxy or acyloxy group, D represents a hydrogen atom, or A and B together can form an acetal or epoxy group, A and D together can form an ethylidene group, and B and D together can form a carbon-carbon direct bond, and the chiral central carbon atoms marked with symbols *, # and ∴ in said formula (I) alternatively have one of an R-configuration and an S-configuration.

Further, in accordance with the present invention, there is provided a process for manufacturing the above compound.

DESCRIPTION OF THE PREFERRED EMBODIMENTS

The process for manufacturing the compound of the general formula (I) according to the present invention includes the following steps.

(a) A step comprising ring-opening an optically active valerolactone compound of the general formula (II):

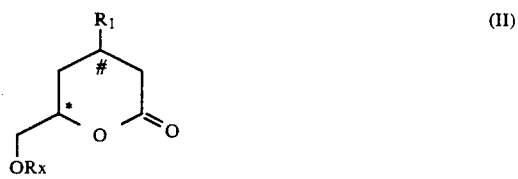

wherein $R_1$ represents a lower alkyl group having 1 to 4 carbon atoms, such as methyl, ethyl, n-propyl or n-butyl group, Rx represents a group for protecting a hydroxy group, preferably a lower alkyl group having 1 to 4 carbon atoms and optionally substituted with one or more lower alkoxy groups having 1 to 4 carbon atoms (such as methyl, methoxymethyl or methoxyethoxymethyl), a benzyl or substituted benzyl group, a substituted phenyl group (such as p-methoxyphenyl), or a silyl group substituted with one or more lower alkyl groups having 1 to 4 carbon atoms (such as t-butyldimethylsilyl), and the symbols * and # have the same meanings as above, to thereby obtain an optically active corresponding hydroxyhexanoic acid compound of the general formula (Ia):

wherein $R_1$, Rx, and the symbols * and # have the same meanings as above, and Ra represents a lower alkyl group having 1 to 4 carbon atoms, while retaining the R-configuration or S-configuration of the chiral central carbon atoms marked with the symbols * and # in said formula (II).

(b) A step comprising protecting the hydroxy group in the optically active hydroxyhexanoic acid compound of the general formula (Ia), to thereby obtain an optically active corresponding protected hydroxyhexanoic acid compound of the general formula (Ib):

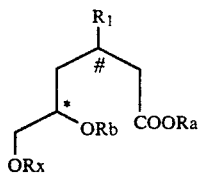
(Ib)

wherein $R_1$, Ra, Rx, and the symbols * and # have the same meanings as above, and Rb represents a group for protecting a hydroxy group, preferably the groups as mentioned referring to said group Rx, while retaining the S-configuration or R-configuration alternatively possessed by the chiral central carbon atoms * and #.

(c) A step comprising reducing the optically active protected hydroxyhexanoic acid compound of the general formula (Ib), to thereby obtain an optically active corresponding hexylalcohol compound of the general formula (Ic):

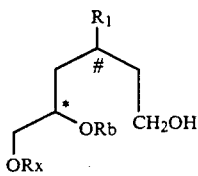
(Ic)

wherein $R_1$, Rb, Rx, and the symbols * and # have the same meanings as above, while retaining the S-configuration or R-configuration alternatively possessed by the chiral central carbon atoms * and #.

(d) A step comprising protecting the hydroxy group in the optically active hexylalcohol compound of the general formula (Ic), to thereby obtain an optically active corresponding hexylether compound of the general formula (Id):

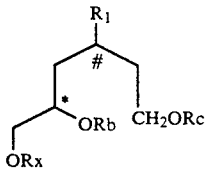
(Id)

wherein $R_1$, Rb, Rx, and the symbols * and # have the same meanings as above, and Rc represents a group for protecting a hydroxy group, preferably the groups as mentioned referring to said group Rx, while retaining the S-configuration or R-configuration alternatively possessed by the chiral central carbon atoms * and #.

(e) A step comprising reacting the optically active hexylether compound of the general formula (Id) with an alkyl magnesium halide of the general formula (III):

Rd-MgX¹ (III)

wherein Rd represents a straight-chain or branched alkyl group having 1 to 6 carbon atoms, such as methyl, ethyl, propyl or butyl, preferably isobutyl group, and $X^1$ represents a halogen atom, such as chlorine, bromine or iodine atom, to thereby obtain an optically active corresponding alkyl-substituted hexane compound of the general formula (Ie):

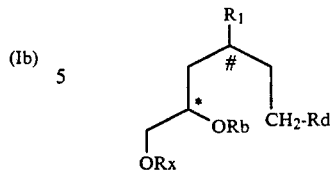
(Ie)

wherein $R_1$, Rb, Rd, Rx and the symbols * and # have the same meanings as above, while retaining the S-configuration or R-configuration alternatively possessed by the chiral central carbon atoms * and #.

(f) A step comprising removing the protecting group in the optically active alkyl-substituted hexane compound of the general formula (Ie), to thereby obtain an optically active corresponding alkyldiol compound of the general formula (If):

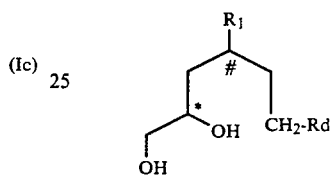
(If)

wherein $R_1$, Rd and the symbols * and # have the same meanings as above, while retaining the S-configuration or R-configuration alternatively possessed by the chiral central carbon atoms * and #.

(g) A step comprising reacting the optically active alkyldiol compound of the general formula (If) with an aldehyde compound of the general formula (IV):

Re-CHO (IV)

wherein Re represents a substituted or unsubstituted aromatic group, such as phenyl group, to thereby obtain an optically active corresponding alkylacetal compound of the general formula (Ig):

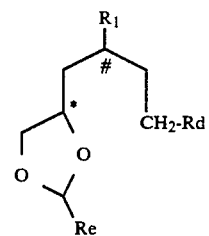
(Ig)

wherein $R_1$, Rd, Re and the symbols * and # have the same meanings as above, while retaining the S-configuration or R-configuration alternatively possessed by the chiral central carbon atoms * and #.

(h) A step comprising treating the optically active alkylacetal compound of the general formula (Ig) with a halogenating agent, to thereby obtain an optically active corresponding acyloxyalkane compound of the general formula (Ih):

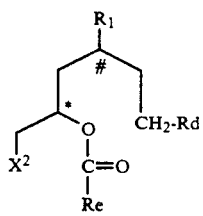
(Ih)

wherein $R_1$, Rd, Re and the symbols * and # have the same meanings as above, and $X^2$ represents a halogen atom, for example, those as mentioned referring to the group $X^1$, while retaining the S-configuration or R-configuration alternatively possessed by the chiral central carbon atoms * and #.

(i) A step comprising epoxidizing the optically active acyloxyalkane compound of the general formula (Ih), to thereby obtain an optically active corresponding epoxyalkane compound of the general formula (Ii):

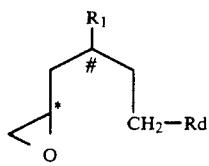
(Ii)

wherein $R_1$, Rd and the symbols * and # have the same meanings as above, while retaining the S-configuration or R-configuration alternatively possessed by the chiral central carbon atoms * and #.

(j) A step comprising reacting the optically active epoxyalkane compound of the general formula (Ii) with a metallic acetylide, to thereby obtain an optically active corresponding α,β-alkyne compound of the general formula (Ij):

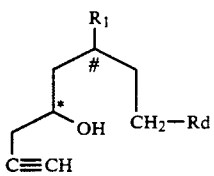
(Ij)

wherein $R_1$, Rd and the symbols * and # have the same meanings as above, while retaining the S-configuration or R-configuration alternatively possessed by the chiral central carbon atoms * and #.

The steps (a) to (j) and so on will be described hereinafter in detail.

Step (a)

The ring-opening by esterifying the valerolactone compound (II) is carried out at 0° C. to 100° C., preferably at room temperature, in a hydrophilic solvent, such as methyl alcohol, ethyl alcohol or benzyl alcohol, in the presence of an alkali metal carbonate (such as potassium carbonate) or alkali metal alkoxide.

The configurations of the 3 and 5-chiral central carbon atoms stemming from the valerolactone compound (II) are unchanged in this step (a), and retained in the resulting hydroxyhexanoic acid compound (Ia).

The resulting compound (Ia) may be used in the next step (b) without further purification, or after purification (for example, by silica gel column chromatography) if necessary.

The valerolactone compound (II) used in this step (a) as the starting material may be prepared, for example, by the following processes:

In the first step, an optically active (S) or (R)-glycidol compound of the general formula (V):

(V)

wherein $R_1$ and the symbol * have the same meanings as above, is reacted with a propargylic acid or a derivative thereof having the general formula (VI):

(VI)

$$HC\equiv C-COOR_y$$

wherein Ry represents a hydrogen atom; an alkyl group, preferably a lower alkyl group having 1 to 4 carbon atoms (such as methyl or ethyl group); a phenyl-substituted alkyl group, preferably a lower alkyl group having 1 to 4 carbon atoms substituted with a phenyl group (such as benzyl group); an alkenyl group, preferably a lower alkenyl group having 1 to 4 carbon atoms (such as allyl group); phenyl group; a substituted phenyl group, preferably a phenyl group substituted by one or more lower alkyl or alkoxy group having 1 to 4 carbon atoms (such as p-methoxy group); or trialkylsilyl group, preferably tri-lower alkylsilyl group (such as trimethylsilyl group), to thereby obtain an optically active corresponding (S) or (R).hexynoate compound of the general formula (VII):

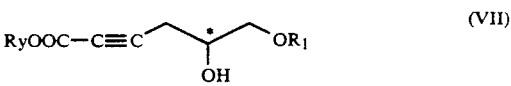
(VII)

wherein $R_1$, Ry and the symbol * have the same meanings as above, while retaining the S-configuration or R-configuration alternatively possessed by the chiral central carbon atom *.

The starting glycidol compound (V) contains a chiral center *, and thus includes an S-form and an R-form. Each of glycidol compound (V) in the S-form and the R-form is known.

The reaction of the glycidol compound (V) and the propargylic acid or the derivative thereof (VI) is carried out in an atmosphere of an inert gas (such as an argon or nitrogen gas), at a low temperature (for example, 0° C. to 120° C., preferably .10° C. to 100° C.), in an aprotic solvent (such as tetrahydrofuran, toluene, hexane or ether), in the presence of a strong base (such as alkyl lithium) and Lewis acid catalyst (such as boron trifluoride, particularly boron trifluoride ether). By this reaction, the configuration of the chiral central carbon atom * stemming from the starting glycidol compound (V) is introduced into the resulting hexynoate compound (VII). The resulting compound may be purified by silica gel column chromatography.

Then, after absorbing 1 molar equivalent of hydrogen under an ordinary pressure in the presence of Lindlar catalyst, the hexynoate compound (VII) is heated in toluene, to thereby obtain an optically active corresponding (S) or (R)-unsaturated valerolactone compound of the general formula (VIII):

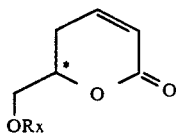

(VIII)

wherein Rx and the symbol * have the same meanings as above, while retaining the S-configuration or R-configuration alternatively possessed by the chiral central carbon atom *.

By this reaction, the configuration of the 5-chiral central carbon atom * stemming from the hexynoate compound (VII) is unchanged and introduced into the 5-position of the resulting unsaturated valerolactone compound (VIII).

The resulting compound may be used in the next step after purification by silica gel column chromatography, if necessary.

In the next step, the unsaturated valerolactone compound (VIII) is reacted with a nucleophilic agent of the general formula (IX):

$$M^I M^{II}(R_1)_2 \quad \text{(IX)}$$

wherein $M^I$ represents a univalent metallic ion, such as lithium or copper ion, $M^{II}$ represents a divalent metallic ion, such as copper or magnesium ion, and $R_1$ has the same meaning as above, to thereby obtain an optically active corresponding valerolactone compound of the general formula (II), while retaining the S-configuration or R-configuration alternatively possessed by the chiral central carbon atom *.

The above step is carried out in an atmosphere of an inert gas (such as an argon or nitrogen gas), at a low temperature (for example, 0° C. to −100° C., preferably −10° C. to −80° C.), in an aprotic solvent (such as tetrahydrofuran, toluene, hexane or ether), in the presence of a copper (I) compound (such as CuI, CuCN). As examples of the nucleophilic agent, there may be mentioned lithium dialkylcuprate, lithium diphenylcuprate, alkyl or phenyl magnesium halide.

By this reaction, the configuration of the 5-chiral central carbon atom * stemming from the hexynoate compound (VII) is unchanged and introduced into the 5-position of the resulting valerolactone compound (II). Further, a new chiral center # is introduced into the resulting valerolactone compound (II). The configuration of the new chiral center # is dependent upon that of the 5-chiral central carbon atom * in the unsaturated valerolactone compound (VIII). More particularly, the 3-alkyl group is introduced selectively in the anti-side to the 5-substituent.

The resulting compound is used in the next step (a), after purification by silica gel column chromatography, if necessary.

Step (b)

The protection of the hydroxy group is carried out at 0° C. to 50° C., preferably at room temperature, in an aprotic solvent (such as dimethylformamide) or an ethereal solvent (such as ethylether or tetrahydrofuran), using trialkylsilyl halide.

The configurations of two chiral central carbon atoms * and # stemming from the hydroxyhexanoic acid compound (Ia) are unchanged in this step (b), and retained in the resulting protected hydroxyhexanoic acid compound (Ib).

The resulting compound (Ib) is used in the next step, after purification (for example, by silica gel column chromatography) if necessary.

Step (c)

The reduction of the ester moiety is carried out at a low or ordinary temperature (for example, −10° C. to 30 ° C., particularly 0° C. to +10° C.) in an ethereal solvent (for example, tetrahydrofuran, ether or dioxane), using a hydride reducing agent (such as lithium aluminum hydride).

The configurations of two chiral central carbon atoms * and # stemming from the protected hydrohexanoic acid compound (Ib) are unchanged in this step (c), and retained in the resulting hexylalcohol compound (Ic).

The resulting compound (Ic) is used in the next step (d), after purification (for example, by silica gel column chromatography) if necessary.

Step (d)

The esterification of the hydroxy group to the sulfonate is carried out at a low or ordinary temperature (for example, −10° C. to +30° C., particularly 0° C. to room temperature) in an aprotic solvent (for example, alkyl halide, such as dichloromethane, ether or tetrahydrofuran), in the presence of a tertiary amine (such as pyridine, triethylamine or 4-N,N-dimethylaminopyridine), using an alkyl or aromatic sulfonic acid chloride (such as methanesulfonic acid chloride or toluenesulfonic acid chloride).

The configurations of two chiral central carbon atoms * and # stemming from the hexylalcohol compound (Ic) are unchanged in this step (d), and retained in the resulting hexylether compound (Id).

The resulting compound (Id) is used in the next step (e), after purification (for example, by silica gel column chromatography) if necessary.

Step (e)

The reaction of the hexylether compound (Id) and the alkyl magnesium halide (III) is carried out at a low temperature (for example, −78° C. to +10° C., particularly 0° C. to+5° C.) in an ethereal solvent (for example, ether or tetrahydrofuran), in the presence of a copper salt (such as cuprous iodide or cuprous cyanide), using an alkyl or aromatic lithium compound or an alkyl or aromatic magnesium halide.

The configurations of two chiral central carbon atoms * and # stemming from the hexylether compound (Id) are unchanged in this step (e), and retained in the resulting alkyl-substituted hexane compound (Ie).

The resulting compound (Ie) is used in the next step (f), after purification (for example, by silica gel column chromatography) if necessary.

Step (f)

The elimination of the protecting group is carried out at an ordinary or elevated temperature (for example, room temperature to+50° C., particularly room temperature) in an alcoholic solvent (for example, methanol or ethanol), in the presence of a palladium catalyst (such as palladium hydroxide or palladium on charcoal), under hydrogen stream.

The configurations of two chiral central carbon atoms * and # stemming from the alkyl-substituted hexane compound (Ie) are unchanged in this step (f), and retained in the resulting alkyldiol compound (If).

The resulting compound (If) is used in the next step (g), after purification (for example, by silica gel column chromatography) if necessary.

Step (g)

As the aromatic aldehyde compound (IV), there may be used benzaldehyde compound, for example, paramethoxy benzaldehyde, particularly benzaldehyde. The reaction is carried out at an elevated temperature (for example, 80° C. to 100° C.), in an azeotropic solvent (such as benzene or toluene).

The configurations of two chiral central carbon atoms * and # stemming from the alkyldiol compound (If) are unchanged in this step (g), and retained in the resulting aromatic acetal compound (Ig).

The resulting compound (Ig) is used in the next step (h), after purification (for example, by silica gel column chromatography) if necessary.

Step (h)

The cleavage of the acetal moiety is carried out at 0° C. to 40° C., particularly 10° C. to 20° C., in a halogenated hydrocarbon solvent (such as carbon tetrachloride or dichloromethane), preferably using N-halogenated carboxylic acid imide (for example, N-bromosuccinic acid imide).

The configurations of two chiral central carbon atoms * and # stemming from the aromatic acetal compound (Ig) are unchanged in this step (h), and retained in the resulting acyloxyalkane compound (Ih).

The resulting compound (Ih) may be used in the next step (i) without purification, or after purification (for example, by silica gel column chromatography) if necessary.

Step (i)

The epoxidation is carried out at an ordinary temperature (for example, +10° C. to +20° C.), with stirring, in an alcoholic solvent (such as hydrous methanol), in the presence of an alkali hydroxide (for example, sodium or potassium hydroxide).

The configurations of two chiral central carbon atoms * and # stemming from the acyloxyalkane compound (Ih) are unchanged in this step (i), and retained in the resulting epoxyalkane compound (Ii).

The resulting compound (Ii) may be used in the next step (i) without purification, or after purification (for example, by silica gel column chromatography) if necessary.

Step (j)

The introduction of the terminal acetylene group is carried out at a low or ordinary temperature (for example, 0° C. to +30° C., preferably about 20° C.), in a polar solvent (such as dimethyl sulfoxide), using metal acetylide, such as lithium acetylide/ethylenediamine complex.

The configurations of two chiral central carbon atoms * and # stemming from the epoxyalkane compound (Ii) are unchanged in this step (j), and retained in the resulting terminal alkyne compound (Ij).

Step (k)

The unsaturated bond in the optically active terminal alkyne compound of the general formula (Ij) is rearranged, to thereby obtain an optically active corresponding internal alkyne compound of the general formula (X):

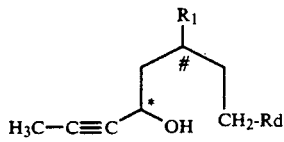
(X)

wherein R₁, Rd and the symbols * and # have the same meanings as above, while retaining the S-configuration or R-configuration alternatively possessed by the chiral central carbon atoms * and #. This step may be carried out by the procedure described in, for example, Takano, et al, Synthesis, 811 (1986).

The product of the step (k) may be reduced to the Z-olefin by the procedure described in, for example, Chan, et al, J. Org. Chem., 41, 3497 (1976), and then, derived to the side chain of vitamin E, using Claisen rearrangement Further, the inventors of the present invention found the other pathway to derive the side chain of vitamin E from the internal alkyne compound (X) obtained in the step (k). The other pathway comprises the following steps (m) to (p):

Step (m)

The optically active internal alkyne compound of the general formula (X) is catalytically hydrogenated, to thereby obtain an optically active corresponding Z-alkene compound of the general formula (XI):

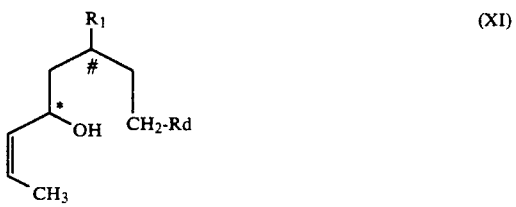

wherein R₁, Rd and the symbols * and # have the same meanings as above, while retaining the S configuration or R-configuration alternatively possessed by the chiral central carbon atoms * and #. This step (m) may be carried out by the procedure described in, for example, Takano, et al, Synthesis, 811 (1986).

Step (n)

The optically active Z-alkene compound of the general formula (XI) is reacted with a halide compound of the general formula (XII):

(XII)

wherein Rf represents an alkyl group and X³ represents a halogen atom, such as chlorine, bromine or iodine atom, to thereby obtain an optically active corresponding trialkylstannylmethyloxyalkene compound of the general formula (Ik):

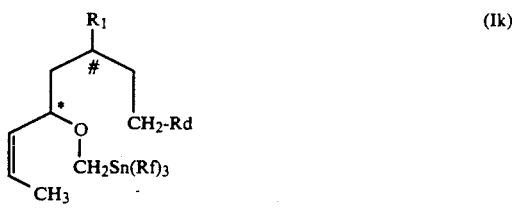
(Ik)

wherein R₁, Rd, Rf and the symbols * and # have the same meanings as above, while retaining the S-configuration or R-configuration alternatively possessed by the chiral central carbon atoms * and #.

The reaction of the step (n) is carried out at −20° C. to 10° C., preferably −5° C. to 0° C., in an ethereal solvent (such as tetrahydrofuran or ether), using alkali metal hydride (such as potassium hydride).

The configurations of two chiral central carbon atoms * and # stemming from the Z-alkene compound (XI) are unchanged in this step (n), and retained in the resulting trialkylstannylmethyloxyalkene compound (Ik).

The resulting compound (Ik) is used in the next step (o), after purification (for example, by silica gel column chromatography) if necessary.

Step (o)

The optically active trialkylstannylmethyloxyalkene compound of the general formula (Ik) is treated with an alkyl lithium, to thereby obtain, via an unstable β,γ-alkene anion compound of the general formula (Im):

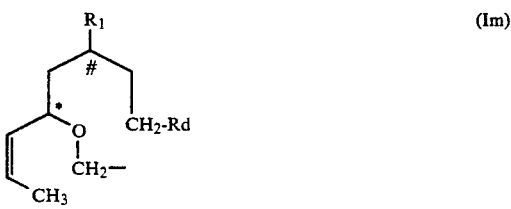

(Im)

wherein $R_1$, Rd and the symbols * and # have the same meanings as above, while retaining the S-configuration or R-configuration alternatively possessed by the chiral central carbon atoms * and #, an optically active corresponding γ,δ-alkene compound of the general formula (In):

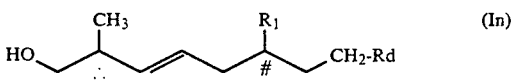

(In)

wherein $R_1$, Rd and the symbols # and ∴ have the same meanings as above, while retaining the S configuration or R-configuration alternatively possessed by the chiral central carbon atom #.

In this step (o), the chiral center * disappears, but a new chiral center → is introduced. The configuration of the new chiral center → is dependent upon that of the disappearing chiral center *. More particularly, the hydroxymethyl group is rearranged in the same direction to the configuration of the disappearing chiral central oxygen atom *, and thus the new chiral center ∴ is formed.

In the step (o), the γ, δ-alkene compound (In) may be obtained by treating the compound (Ik) at a low temperature (for example, −100° C. to 0° C., preferably −70° C. to 50° C.), in an ethereal solvent (such as ether or tetrahydrofuran), in the presence of an alkali lithium (such as n-butyl lithium or methyl lithium).

From the product obtained in the step (o), the side chain of vitamin E may be derived by direct reduction thereof, for example, by the procedure disclosed in Scott, et al, Helv. Chim. acta., 59, 290 (1976); or Chan, et al, JOC., 43, 3435 (1978).

According to the present invention, novel intermediates are provided, which may be prepared from an easily available methyllactone having an optical activity, and from which the side chain of the naturally occurring α-tocopherol can stereoselectively be derived. The intermediate compound of the present invention can be easily and safely prepared, because neither a resolution procedure nor poisonous reagents are required in the process for the manufacture thereof. Further, according to the present invention, the intermediates can be highly stereoselectively be manufactured.

EXAMPLES

The present invention now will be further illustrated by, but is by no means limited to, the following Examples.

EXAMPLE 1: PREPARATION OF METHYL (3S,5R)-6-benzyloxy-5-hydroxy-3-methylhexanoate

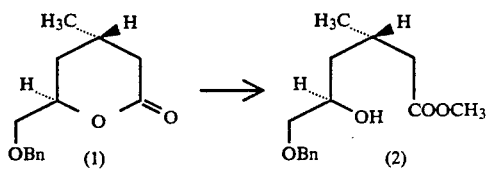

In the formulae mentioned hereinbefore and hereinafter, Bn represents benzyl.

To a solution of methyl lactone compound (1) [1.6 g; 6.8 mmol] in 10 ml of methyl alcohol, 2.0 g (14.5 mmol) of potassium carbonate was added, and the whole was stirred at room temperature for 3 hours. The reaction solution was diluted with dimethylether, and 5% aqueous solution of hydrochloric acid was added thereto. The organic layer was washed with an aqueous saturated solution of sodium hydrogencarbonate and then an aqueous saturated solution of sodium chloride. The residue was dried over anhydrous magnesium sulfate. Thereafter, the solvent was evaporated under reduced pressure to obtain 1.75 g of crude ester compound (2). The physicochemical data are as follows:

IR$\nu$ (neat) max cm$^{-1}$: 3350, 1735.

$^1$H NMR (CDCl$_3$) δ: 7.33 (s, 5H), 4.56 (s, 2H), 3.66 (s, 3H), 3.64 (m, 1H), 3.48 (m, 2H), 2.28 (m, 2H), 1.80 (m, 2H), 1.00 (d, 3H, J =6.5 Hz).

MS m/e: 266 (M+), 91 (100%).

Exact mass:

Calculated for C$_{15}$H$_{22}$O$_4$ (M+): 266.1518,

Found : 266.1496.

The lactone compound (1) used as the starting material in Example 1 was prepared as follows:

To a solution of 2.50 ml (28.1 mmol) of methyl propargylate in 70 ml of tetrahydrofuran, 18.0 ml (28.0 mmol) of n-butyl lithium (1.56 mol solution in n-hexane) was added dropwise at −90° C. over 40 minutes Thereafter, the whole was stirred further for 20 minutes. At the same temperature, a solution of 3.55 g (21.6 mmol) of (S)—O—benzylglycidol in 20 ml of tetrahydrofuran was added by a cannula, and the whole was stirred for 5 minutes. To the resulting yellowish brown solution, 3.50 ml (28.0 mmol) of boron trifluoride/diethylether was added dropwise over 10 minutes, and then, the whole was stirred for 1 hour at the same temperature.

To the resulting reaction solution, 20 ml of an aqueous saturated solution of ammonium chloride was added, and the whole was heated to room temperature, and then, extracted with 200 ml of diethylether. The organic layer was washed with 20 ml of an aqueous saturated solution of sodium hydrogencarbonate and then 20 ml of an aqueous saturated solution of sodium chloride, and dried over anhydrous magnesium sulfate. Thereafter, the solvent was evaporated under reduced pressure.

The residue was treated by silica gel column chromatography (200 g of silica gel was used), 4.50 g (yield: 84

%) of (R)-methyl-6-benzyloxy-5-hydroxy-2-hexynoate [hereinafter referred to as 2-hexynoate compound] was obtained from the diethylether/n-hexane (1:1) effluent. The physicochemical data of 2-hexynoate compound are as follows:

$[\alpha]_D^{29} = -14.7°$ (c=1.07, CHCl$_3$).

Boiling point: 160° to 165° C. (0.3 mmHg) (Kugelrohl).

$^1$H-NMR (CDCl$_3$) δ: 2.60 (2H, d, J=6.0 Hz), 2.60 (1H, brs, disappear with D$_2$O), 3.40-3.75 (2H, m), 3.78 (3H, s), 3.90-4.10 (1H, m), 4.58 (2H, s), 7.3 (5H, s).

IRv (neat) max cm$^{-1}$: 3330 (br), 2260, 1710.

MS m/e: 248 (M$^+$), 91 (100%).

Elementary analysis: Calculated for C$_{14}$H$_{16}$O$_4$: C=67.71; H=6.50, Found : C=67.66; H=6.76.

Subsequently, 7.90 g of 2-hexynoate compound was dissolved in 300 ml of benzene, and 15 drops of quinoline were added. To the resulting mixture, 380 mg of Lindlar catalyst was suspended, and then, 1 molar equivalent of hydrogen was absorbed at room temperature under normal pressure. After the reaction was completed, the catalyst was filtered off. The filtrate was washed with 5% hydrochloric acid and an aqueous saturated solution of sodium hydrogencarbonate, and dried over anhydrous magnesium sulfate. The solvent was evaporated under reduced pressure to obtain 6.59 g of colorless oil. The oil was dissolved in 200 ml of toluene. After adding 300 mg of pyridinium p-toluenesulfonate, the whole was heated for 1 hour under reflux. The solvent was evaporated under reduced pressure. The residue was purified by column chromatography (silica gel) to obtain 5.3 g (80% in total) of α,β-unsaturated lactone compound from the ether/hexane (2:1) effluent.

$[\alpha]_D^{25} = +7.0°$ (c=1.0, CHCl$_3$).

Copper iodide (1.57 g; 8.24 mmol) was suspended in absolute diethylether, and 15.0 ml (16.5 mmol) of methyl lithium (1.09M in diethylether) was added dropwise while cooling with ice. After stirring for 30 minutes at the same temperature, a solution of 598 mg (2.75 mmol) of the above-mentioned α,β-unsaturated lactone compound in 5 ml of absolute diethylether was added dropwise, and the whole was stirred for 30 minutes at the same temperature. After adding an aqueous saturated solution of ammonium chloride, the reaction solution was extracted with diethylether. The organic layer was washed with an aqueous saturated solution of sodium hydrogencarbonate and then an aqueous saturated solution of sodium chloride, and dried over anhydrous magnesium sulfate. The solvent was evaporated under reduced pressure, and the resulting residue was treated by silica gel column chromatography to obtain 474 mg (yield: 74%) of methyllactone compound (1) from the diethylether/hexane (1:1, v/v). The physicochemical data are as follows:

$[\alpha]_D^{25} = -33.33°$ (c=1.014, CHCl$_3$).

IRv (neat) max cm$^{-1}$: 2950, 1735, 1230, 1080, 740, 700.

$^1$H NMR (CDCl$_3$) δ: 7.35 (m, 5H), 4.75 (s, 2H), 4.74-4.40 (m, 1H), 3.64 (dd, 1H, J=11.0, 5.2 Hz), 3.59 (dd, 1H, J=11.0, 5.2 Hz), 2.58 (dd, 1H, J=16.6, 9.2 Hz), 1.97 (ddd, 1H, J=14.8, 7.7, 5.5 Hz), 1.59 (ddd, 1H, J=14.8, 7.4, 4.8 Hz), 1.08 (d, 3H, J=6.3 Hz).

MS m/e: 234 (M$^+$), 91 (100%).

Elementary analysis:

Calculated for C$_{14}$H$_{18}$O$_3$: C=71.77; H=7.74, Found : C=71.68; H=7.80.

EXAMPLE 2: PREPARATION OF METHYL (3S,5R)-6-benzyloxy-5-t-butyldimethylsiloxy-3-methylhexanoate

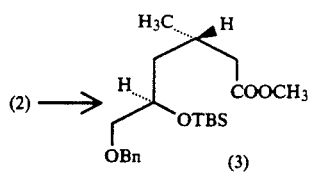

In the formulae mentioned hereinbefore and hereinafter, TBS represents t-butyldimethylsilyl.

Imidazol (1.75 g; 25.72 mmol) and t-butyl dimethylsilylchloride (1.93 g; 12.86 mmol) were added to a solution of 1.75 g of the crude ester compound (2) in 20 ml of dimethylformamide, and stirred at room temperature for 15 hours. The reaction solution was diluted with diethylether, washed with an aqueous saturated solution of sodium bicarbonate and then an aqueous saturated solution of sodium chloride, and dried over anhydrous magnesium sulfate. The solvent was evaporated under reduced pressure. The residue was treated by silica gel column chromatography to obtain 1.9 g (76 %) of the above-mentioned silyl compound (3) from the diethylether/hexane (1:5, v/v) effluent- The physicochemical data are as follows:

$[\alpha]_D^{30} = +8.84°$ (c=0.996, CHCl$_3$).

IRv (neat) max, cm$^{-1}$: 1735.

$^1$H-NMR (CDCl$_3$) δ: 7.32 (s, 5H), 4.52 (s, 2H), 3.90 (m, 1H), 3.65 (s, 2H), 3.38 (d, 2H, J=5.4 Hz), 2.5-2.0 (m, 2H), 0.98 (m, 2H), 0.95 (d, 3H, 6.4 Hz), 0.88 (s, 9H), 0.06 (s, 6H).

MS m/e: 380 (M$^+$), 91 (100%).

Exact mass:

Calculated for C$_{20}$H$_{33}$O$_3$Si(M$^+$ −31): 349.2199, Found : 349.2201.

EXAMPLE 3: PREPARATION OF (3R,5R)-6-benzyloxy-5-t-butyldimethylsiloxy-3-methylhexane-1-ol

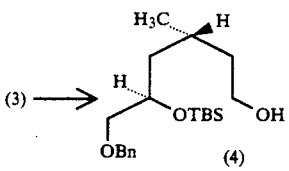

A solution of 1.9 g (5 mmol) of the silylester compound (3) in 5 ml of absolute tetrahydrofuran was added to a solution of 379 mg (10 mmol) of lithium aluminum hydride in 40 ml of absolute tetrahydrofuran while cooling with ice, and stirred at the same temperature for 10 minutes. A concentrated aqueous solution of ammonium hydroxide was added to the reaction solution, and stirred at room temperature for 3 hours. The reaction solution was filtered with celite, and the solvent was evaporated from the filtrate under reduced pressure. The residue was treated by silica gel column chromatography to obtain 1.75 g (99 %) of the above-mentioned alcohol compound (4) from the diethylether/hexane (1:2, v/v) effluent. The physicochemical data are as follows: $[\alpha]_D^- = +5.49°$ (c=1.03, CDCl$_3$).

IRv (neat) max, cm$^{-1}$: 3350.

$^1$H-NMR (CDCl$_3$) δ: 7.32 (s, 5H), 4.53 (s, 2H), 3.90 (m, 1H), 3.65 (m, 2H), 3.39 (d, 2H, J=5.1 Hz), 1.8 1.1 (m, 5H), 0.94 (d, 3H, J=4.9 Hz), 0.88 (s, 9H), 0.062 (s, 6H).

MS m/e: 353 (M+), 91 (100%).

Exact mass:
Calculated for C$_{20}$H$_{36}$O$_3$Si(M+ +1): 353.2500,
Found : 353.2514.

EXAMPLE 4: PREPARATION OF (2R,4R)-1-benzyloxy-2-t-butyldimethylsiloxy-4-methyl-6-tosyloxyhexane

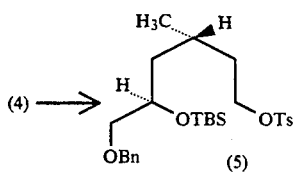

In the formulae mentioned hereinbefore and hereinafter, Ts represents tosyl.

Triethylamine (2.76 mg; 19.9 mmol) and tosyl chloride (1.9 g; 9.9 mmol) were added to a solution of 1.75 g (4.97 mmol) of the alcohol compound (4) in 45 ml of dichloromethane while cooling with ice, and stirred at room temperature for 20 hours. The reaction solution was diluted with dichloromethane, and washed with an aqueous saturated solution of sodium bicarbonate and then an aqueous saturated solution of sodium chloride, and dried over anhydrous magnesium sulfate. The solvent was evaporated under reduced pressure. The residue was treated by silica gel column chromatography to obtain 2.9 g of the above-mentioned tosyl compound (5) from the diethylether/hexane (1:10, v/v) effluent. The product was used in the next step without further purification. The physicochemical data of the tosyl compound (5) are as follows:

$[α]_D^{27}$ = +8.08° (c=1.056, CDCl$_3$).

IRv (neat) max, cm$^{-1}$: 2850, 1360, 1170.

$^1$H-NMR (CDCl$_3$) δ: 7.78 (m, 2H), 7.32 (m, 7H), 4.50 (s, 2H), 4.04 (t, 2H, J=6.1 Hz), 3.82 (m, 1H), 3.32 (d, 2H, J=5.4 Hz), 2.43 (s, 3H), 1.90–1.10 (m, 5H), 0.84 (s, 9H), 0.84 (d, 3H, J=5.8 Hz), 0.013 (s, 6H).

MS m/e: 506 (M+), 507 (M+ +1), 91 (100%).

Exact mass:
Calculated for C$_{27}$H$_{43}$O$_5$SiS(M+ +1): 507.2599,
Found : 507.2594.

EXAMPLE 5: PREPARATION OF (2R, 4R)-1-BENZYLOXY-2-T-BUTYLDIMETHYL-SILOXY-4,8-DIMETHYLNONANE

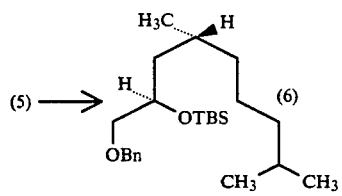

To a solution of Grignard reagent [prepared from 3.2 ml (29.4 mmol) of isobutyl bromide and 823 mg (34.3 mmol) of magnesium]in 90 ml of absolute tetrahydrofuran, a solution of 2.9 g of the tosyl compound (5) in 10 ml of absolute tetrahydrofuran and then 300 mg of copper iodide were added, while cooling with ice. The whole was stirred at the same temperature for 30 minutes. After adding an aqueous saturated solution of ammonium chloride, the reaction solution was extracted with diethylether. The organic layer was washed with an aqueous saturated solution of sodium chloride, and dried over anhydrous magnesium sulfate. The solvent was evaporated under reduced pressure. The residue was treated by silica gel column chromatography to obtain 1.79 g of the above-mentioned alkyl compound (6) [total yield from the alcohol compound (4): 97%] from the hexane effluent. The physicochemical data are as follows:

$[α]_D^{29}$ = +9.63° (c=1.223, CDCl$_3$).

IRv (neat) max, cm$^{-1}$: 2960, 2940, 1460, 1255, 840, 780.

$^1$H-NMR (CDCl$_3$) δ: 7.32 (s, 5H), 4.52 (s, 2H), 3.90 (m, 1H), 3.37 (d, 2H, J=4.9 Hz), 1.6–1.1 (m, 12H), 0.88 (s, 9H), 0.84 (d, 9H, J=4.9 Hz).

MS m/e: 393 (M+ +1), 91 (100%).

Exact mass:
Calculated for C$_{24}$H$_{45}$O$_2$Si(M+ +1): 393.3188,
Found : 393.3192.

EXAMPLE 6: PREPARATION OF (2R,4R)-4,8-dimethylnonane-1,2-diol

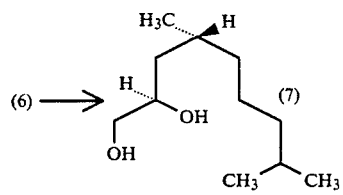

Palladium hydroxide (150 mg) and chloroform (5 ml) were added to a solution of 1.75 g (4.46 mmol) of the diether compound (6) in 20 ml of methyl alcohol, and stirred at room temperature for 6 hours under hydrogen stream. The reaction solution was filtered with celite. The solvent was evaporated from the filtrate under reduced pressure. The residue was treated by silica gel column chromatography to obtain 800 mg (95%) of the above. mentioned diol compound (7) from the diethylether effluent. The physicochemical data are as follows:

$[α]_D^{31}$ = +9.33° (c=1.096, CDCl$_3$).

IRv (neat) max, cm$^{-1}$: 3350, 2960, 2940, 1460.

$^1$H-NMR (CDCl$_3$) δ: 3.90–3.25 (m, 3H), 2.44 (brs, 2H, exchangeable with D$_2$O), 1.70–1.00 (m, 10H), 0.93 (d, 3H, J=5.4 Hz), 0.86 (d, 6H, J=6.1 Hz).

MS m/e: 188 (M+), 57 (100%).

Exact mass:
Calculated for C$_{11}$H$_{24}$O$_2$(M+): 188.1776,
Found : 188.1761.

EXAMPLE 7: PREPARATION OF (2R,4R)-1,2-O-benzylidene-4,8-dimethylnonanone-1,2-diol

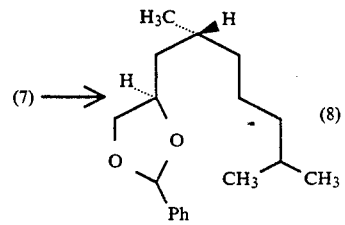

In the formulae mentioned hereinbefore and hereinafter, Ph represents phenyl.

Benzaldehyde (0.46 ml; 4.6 mmol) and p-toluenesulfonic acid (38 mg; 0.2 mmol) were added to a solution of 798 mg (4.24 mmol) of the diol compound (7) in 23 ml of benzene, and heated under reflux for 3 hours. The reaction solution was cooled to room temperature, diluted with diethylether, washed with an aqueous saturated solution of sodium bicarbonate and then an aqueous saturated solution of sodium chloride, and dried over anhydrous magnesium sulfate. The solvent was evaporated under reduced pressure. The residue was treated by silica gel column chromatography to obtain 1.08 g (92%) of the above-mentioned acetal compound (8) from the diethylether/hexane (1:10, v/v) effluent. The physicochemical data are as follows:

IRν (neat) max, cm$^{-1}$: 2950, 2930, 1460, 1380, 1090, 758.

$^1$H-NMR (CDCl$_3$) δ: 7.6-7.3 (m, 5H), 5.93 (s, 1/2H), 5.80 (s, ½ H), 4.4-4.0 (m, 2H), 3.6 (m, 1H), 1.7-1.1 (m, 10H), 0.94 (d, 3H, J=5.4 Hz), 0.86 (d, 6H, J=6.1 Hz).

MS m/e: 276 (M$^+$ −1), 275 (100%).

Exact mass:
Calculated for C$_{18}$H$_{27}$O$_2$(M$^+$ −1) 275.2010,
Found : 275.1996.

EXAMPLE 8: PREPARATION OF
(2R,4R)-1-bromo-4,8-dimethylnonane-2-benzoate

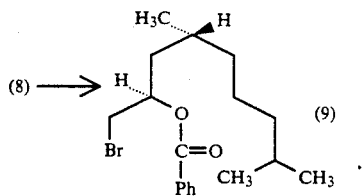

To a solution of 581 mg (2.11 mmol) of the acetal compound (8) in 8 ml of carbon tetrachloride, 1.1 g (6.3 mmol) of n-broxosuccinimide was added at room temperature. The whole was heated for a while by a drier, and stirred at room temperature for 6 hours. The reaction solution was filtered with celite. After adding dichloromethane, the filtrate was washed with an aqueous saturated solution of sodium bicarbonate, then with 10% solution of sodium thiosulfate, and finally with an aqueous saturated solution of sodium chloride, and dried over anhydrous magnesium sulfate. The solvent was evaporated under reduced pressure to obtain 956 mg of the crude bromobenzoate compound (9). The product was used in the next step without further purification. The physicochemical data are as follows:

IRν (neat) max, cm$^{-1}$: 2860, 2840, 1720, 1600, 1270, 710.

$^1$H-NMR (CDCl$_3$) δ: 8.05 (m, 2H), 7.52 (m, 3H), 5.33 (m, 1H), 3.61 (dd, 2H, J=4.2, 2.4 Hz), 1.85-1.10 (m, 10H), 0.95 (d, 3H, J=6.1 Hz), 0.83 (d, 6H, J=6.1 Hz).

MS m/e: 355 (M$^{30}$ +1), 105 (100%).

Exact mass:
Calculated for C$_{18}$H$_{27}$O$_2$Br(M$^+$): 354.1194,
Found : 354.1180.

EXAMPLE 9: PREPARATION OF
(2R,4R)-1,2-epoxy-4,8-dimethylnonane

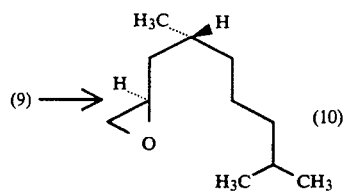

Sodium hydroxide (504 mg; 12.6 xmol), water (2 ml) and methyl alcohol (2 ml) were added to a solution of 956 mg of the crude bromobenzoate compound (9) in 8 ml of tetrahydrofuran, and stirred at room temperature for 6 hours. Diethylether and water were added to the reaction solution, the organic layer was washed with an aqueous saturated solution of sodium chloride, and dried over anhydrous magnesium sulfate. The solvent was evaporated under reduced pressure to obtain 420 mg of the crude epoxy compound (10). The product was used in the next step without further purification. The physicochemical data are as follows:

[α]$_D^{29}$= +13.45° (c=1.568, CDCl$_3$).

IRν (neat) max, cm$^{-1}$: 2950, 2920, 1460.

$^1$H-NMR (CDCl$_3$) δ: 2.94 (m, 1H), 2.74 (t, 1H, J=5.1 Hz), 2.42 (dd, 1H, J=5.1, 2.6 Hz), 1.85-1.10 (m, 10H), 0.97 (d, 3H, J=6.1 Hz), 0.86 (d, 6H, J=6.1 Hz).

MS m/e: 127 (M$^+$ −43), 43 (100%).

EXAMPLE 10: PREPARATION OF
(4R,6R)-6,10-dimethylundec-1-yn-4-ol

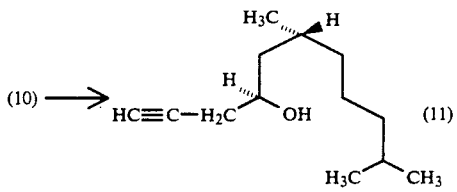

Lithium acetylide ethylenediamine complex (683 mg; 6.3 mmol) was added to a solution of 420 mg of the crude epoxide compound (10) in 6 ml of dimethylsulfoxide, and stirred at room temperature for 6 hours. Diethylether and an aqueous saturated solution of sodium chloride were added to the reaction solution while cooling with ice, the organic layer was washed with a 10% aqueous solution of hydrochloric acid, then an aqueous saturated solution of sodium bicarbonate, and finally an aqueous saturated solution of sodium chloride, and dried over anhydrous magnesium sulfate. The solvent was evaporated under reduced pressure. The residue was treated by silica gel column chromatography to obtain 364 mg [88% from the acetal compound (8)] of the terminal acetylene compound (11) from the diethylether/hexane (1:10, v/v) effluent. The physicochemical data are as follows:

[α]$_D^{28}$= +5.52° (c=1.088, CDCl$_3$).

IRν (neat) max, cm$^{-1}$: 3360, 3300, 2100, 1462.

$^1$H-NMR (CDCl$_3$) δ: 3.86 (m, 1H), 2.37 (m, 2H), 2.06 (t, 1H, J=2.6 Hz), 1.86 (d, 1H, J=5.1 Hz, exchangeable with D$_2$O), 1.7-1.0 (m, 10H), 0.91 (d, 3H, J=5.8 Hz), 0.86 (d, 6H, J=6.1 Hz).

MS m/e: 196 (M$^+$), 57 (100%).

Exact mass

Calculated for C₁₃H₂₄O(M+): 196.1827,
Found : 196.1812.

EXAMPLE 11: PREPARATION OF (4R,6R)-6,10-dimethylundec-2-yn-4-ol

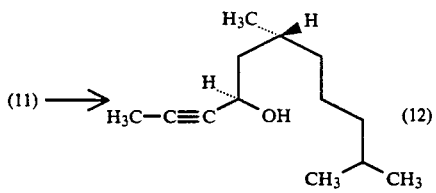

Potassium t-butylate (1.03 g; 9.18 mmol) was added to a solution of 360 mg (1.84 mmol) of the terminal acetylene compound (11) in 5 ml of dimethylsulfoxide at room temperature, and stirred for 20 minutes. Diethylether and water were added to the reaction solution, the organic layer was washed with an aqueous saturated solution of sodium chloride, and dried over anhydrous magnesium sulfate. The solvent was evaporated under reduced pressure. The residue was treated by silica gel column chromatography to obtain 236.2 mg (66%) of the internal acetylene compound (12) from the diethylether/hexane (1:10, v/v) effluent- The physicochemical data are as follows:

$[\alpha]_D^{27} = +10.36°$ (c=2.92, CDCl₃).
IRv (neat) max, cm⁻¹: 3330, 2925, 1462, 1030.
¹H NMR (CDCl₃) δ: 4.43 (m, 1H), 1.84 (d, 3H, J=2.2 Hz), 1.90–1.05 (m, 11H), 0.91 (d, 3H, J=5.8 Hz), 0.86 (d, 6H, J=6.1 Hz).
MS m/e: 195 (M+ −1), 69 (100%).
Exact mass:
Calculated for C₁₃H₂₃O(M+ −1): 195.1749,
Found : 195.1747.

The spectra data of the internal acetylene compound (12) obtained in this Example 11 were substantially identical to those mentioned in K. K. Chan, et al, J. Org., Chem., 41, 3497 (1976).

EXAMPLE 12: PREPARATION OF (4R,6R)-Z-6,10-dimethylundec-2-en-4-ol

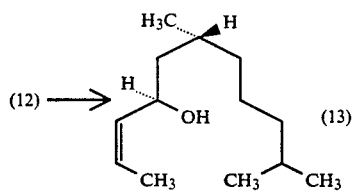

Quinoline (0.01 ml) and Lindlar catalyst (23 mg) were added to a solution of 230 mg (1.173 mmol) of the internal acetylene compound (12) in 3 ml of hexane, and stirred under hydrogen stream at room temperature for 1 hour. The reaction solution was filtered with celite, the filtrate was diluted with diethylether, washed with a 10% aqueous solution of hydrochloric acid, then an aqueous saturated solution of sodium bicarbonate, and finally an aqueous saturated solution of sodium chloride, and dried over anhydrous magnesium sulfate. The solvent was evaporated under reduced pressure. The residue was treated by silica gel column chromatography to obtain 208 mg (90%) of the Z-olefin compound (13) from the diethylether/hexane (1:20, v/v) effluent- The physicochemical data are as follows:

$[\alpha]_D^{25} = +19.95°$ (c=3.22, CDCl₃).

IRv (neat) max, cm⁻¹: 3330, 2960, 2940, 1462, 1010.
¹H NMR (CDCl₃) δ: 5.8–5.2 (m, 2H), 4.60 (m, 1H), 1.69 (dd, 3H, J=6.3, 1.2 Hz), 1.7–1.1 (m, 11H), 0.91 (d, 3H, J=5.8 Hz), 0.86 (d, 6H, J=6.1 Hz).
MS m/e: 198 (M+), 71 (100%).
Exact mass:
Calculated for C₁₃H₂₆O(M+): 198.1984,
Found : 198.2011.

The spectra data of the Z-olefin compound (13) obtained in this Example 12 were substantially identical to those mentioned in K. K. Chan, et al, J. Org., Chem., 41, 3497 (1976).

EXAMPLE 13: PREPARATION OF (4R,6R)-Z-3-(TRIBUTYLSTANNIO)METHOXY-4,8-DIMETHYLUNDEC-2-ENE

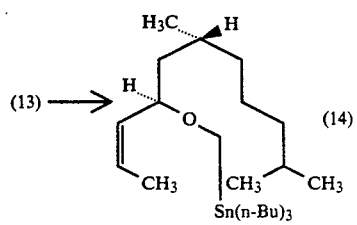

In the above formula, n-Bu represents n-butyl.

A solution of 161 mg (0.813 mmcl) of the Z-olefin compound (13) in 1 ml of absolute tetrahydrofuran was added to a solution of 97.9 mg (2.44 mmol) of potassium hydride in 4 ml of absolute tetrahydrofuran while cooling with ice, and stirred at room temperature for 30 minutes. Further, a solution of 700 mg (1.626 mmol) of tri-n-butylstannylmethane iodide in 2 ml of absolute tetrahydrofuran was added and stirred at the same temperature for 3 hours. Diethylether and water were added to the reaction solution, the organic layer was washed with an aqueous saturated solution of sodium chloride, and dried over anhydrous magnesium sulfate. The solvent was evaporated under reduced pressure. The residue was treated by silica gel column chromatography to obtain 308 mg (78%) of the ether compound (14) from the diethylether/hexane (1:100, v/v) effluent- The physicochemical data are as follows:

$[\alpha]_D^{28} = +1.77°$ (c=2.32, hexane).
IRv (neat) max, cm⁻¹: 2960, 2940, 1460, 1378, 1045.
¹H-NMR (CDCl₃) δ: 5.65 (m, 1H), 5.18 (m, 1H), 3.90 (m, 1H), 3.77 (d, 1H, J=10.3 Hz), 3.41 (d, 1H, J=10.3 Hz), 1.68 (dd, 3H, J=6.7, 1.5 Hz), 1.8–1.0 (m, 22H), 1.0–0.8 (m, 21H).
MS m/e: 445 (M+ −59), 291 (100%).
Exact mass:
Calculated for C₂₂H₄₆OSn(M+ −59): 445.2492,
Found : 445.2481.

EXAMPLE 14: PREPARATION OF (2R,6R)-E-2,6,10-trimethylundec-3-ene-1-ol

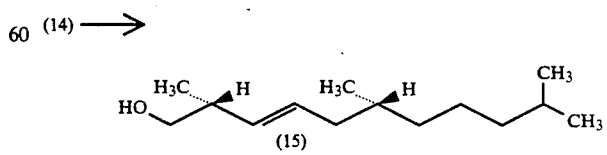

To a solution of 300 mg (0.617 mmol) of the ether compound (14) in 20 ml of absolute tetrahydrofuran, 0.77 ml (1.23 mmol) of n-butyl lithium (1.6M in hexane)

was gradually added at .70° C., and stirred at room temperature for 10 minutes, and further stirred at −20° C. for 30 minutes. After adding an aqueous saturated solution of sodium chloride, the reaction solution was diluted with diethylether. The organic layer was washed with an aqueous saturated solution of sodium bicarbonate and then an aqueous saturated solution of sodium chloride, and dried over anhydrous magnesium sulfate. The solvent was evaporated under reduced pressure. The residue was treated by silica gel column chromatography to obtain 207 mg (77%) of the alcohol compound (15) from the diethylether/hexane (1:4, v/v) effluent- The physicochemical data are as follows:

$[\alpha]_D^{29} = +21.85°$ (c=1.12, hexane).

IRv (neat) max, cm$^{-1}$: 3350, 2960, 2940, 1460, 1038.

$^1$H-NMR (CDCl$_3$) δ: 5.40 (m, 2H), 3.40 (brd, 2H, J=7.1 Hz), 2.32 (dt, 1H, J=13.4, 6.7 Hz), 1.94 (dd, 2H, J=13.4, 5.8 Hz), 1.7–1.05 (m, 9H), 0.85 (d, 12H, J=6.1 Hz), 0.98 (d, 3H, J=6.5 Hz).

MS m/e: 212 (M+), 7 (100%).

Exact mass:

Calculated for C$_{14}$H$_{28}$O(M+): 212.2140,

Found : 212.2122.

EXAMPLE 15: PREPARATION OF (2R,6R)-2,6,10-TRIMETHYLUNDECANE-1-ol

(15) ⟶

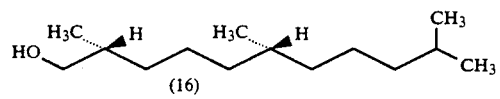

(16)

To a solution of 93 mg (0.44 mmol) of the olefin compound (15) in 7 ml of ethyl acetate, 15 mg of 10% palladium -carbon was added, and stirred at room temperature for 2 hours under hydrogen stream. The reaction solution was filtered with celite, the solvent was evaporated from the filtrate under reduced pressure. The residue was treated by silica gel column chromatography to obtain 75 mg (80%) of the alcohol compound (16) from the diethylether/hexane (1:15, v/v) effluent- The physicochemical data are as follows:

$[\alpha]_D^{27} = +8.78°$ (c=1.2, hexane).

IRv (neat) max, cm$^{-1}$: 3320, 2940, 1460, 1030

$^1$H-NMR (CDCl$_3$) δ: 3.46 (dd, 2H, J=6.1, 2.7 Hz), 1.7–1.0 (m, 16H), 0.92 (d, 3H, J=6.3 Hz), 0.86 (d, 9H, J=6.3 Hz).

$^{13}$C-NMR (CDCl$_3$) δ: 16.71, 19.78, 22.68, 22.77, 24.49, 24.85, 28.04, 32.83, 33.58, 35.86, 37.33, 37.44, 39.43, 68.39.

MS m/e: 196 (M+-H$_2$O), 57 (100%).

The spectra data of the alcohol compound (16) obtained in this Example 15 were substantially identical to those mentioned, for example, in T. Ichikawa, et al, Bull., Chem., Soc., Jpn, 41, 1224 (1968).

Although the present invention has been described with reference to specific embodiments, various changes and modifications obvious to those skilled in the art are deemed to be within the spirit, scope and concept of the invention.

We claim:

1. A process for manufacturing an optically active α,β-alkyne compound of the general formula (Ij):

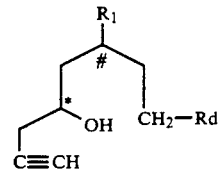

wherein R$_1$ represents a lower alkyl group having 1 to 4 carbon atoms, Rd represents a straight-chain or branched alkyl group having 1 to 6 carbon atoms, and the chiral central carbon atoms marked with symbols * and # in said formula (Ij) alternatively have one of an R-configuration and an S-configuration, said process comprising reacting an optically active epoxyalkane compound of the general formula (Ii):

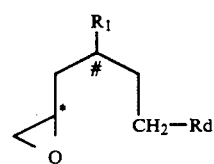

wherein R$_1$, Rd, and the symbols * and # have the same meanings as above, at a temperature of 0° to 30° C. with a metallic acetylide, to thereby obtain the corresponding optically active α,β-alkyne compound of the general formula (Ij) while retaining the R-configuration or S-configuration of the chiral central carbon atoms marked with the symbols * and # in said formula (Ii).

2. The process according to claim 1, wherein said metallic acetylide is lithium acetylide/ethylenediamine complex.

3. A process according to claim 1, wherein said reaction is carried out in dimethylsulfoxide solvent.

4. A process according to claim 1, which further comprises preparing said optically active epoxyalkane compound of the general formula (Ii) by epoxidizing an optically active acyloxyalkane compound of the general formula (Ih):

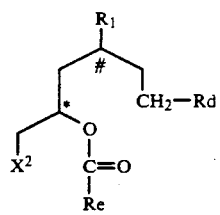

wherein Re represents a substituted or unsubstituted aromatic group, X$^2$ represents a halogen atom, and R$_1$, Rd, and the symbols * and # have the same meanings as above.

5. A process for manufacturing an optically active α,β-alkyne compound of the general formula (Ij):

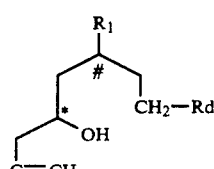

wherein $R_1$ represents a lower alkyl group having 1 to 4 carbon atoms, Rd represents a straight-chain or branched alkyl group having 1 to 6 carbon atoms, and the chiral central carbon atoms marked with symbol * and # in said formula (Ij) alternatively have one of an R-configuration and an S-configuration, said process consists essentially of reacting an optically active epoxyalkane compound of the general formula (Ii):

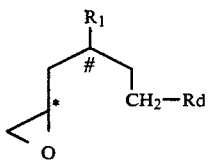
(Ii)

wherein $R_1$, Rd, and the symbols * and # have the same meanings as above, at a temperature of 0° to 30° C. with a metallic acetylide in dimethylsulfoxide solvent, to thereby obtain the corresponding optically active $\alpha,\beta$-alkyne compound of the general formula (Ij) while retaining the R-configuration or S-configuration of the chiral central carbon atoms marked with the symbols * and # in said formula (Ii).

6. A process according to claim 5, wherein said metallic acetylide is lithium acetylide/ethylenediamine complex.

7. A process according to claim 5, which further comprises preparing said optically active epoxyalkane compound of the general formula (Ii) by epoxidizing in a reaction medium comprising water, methyl alcohol and tetrahydrofuran an optically active acyloxyalkane compound of the general formula (Ih):

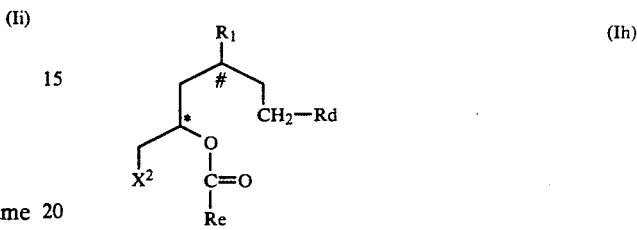

wherein Re represents a substituted or unsubstituted aromatic group, $X^2$ represents a halogen atom, and $R_1$, Rd, and the symbols * and # have the same meanings as above.

* * * * *

UNITED STATES PATENT AND TRADEMARK OFFICE
CERTIFICATE OF CORRECTION

PATENT NO. : 5,243,096
DATED : September 7, 1993
INVENTOR(S) : Seiichi Takano, et. al.

It is certified that error appears in the above-indentified patent and that said Letters Patent is hereby corrected as shown below:

Claim 5, Column 23, line 5, delete "symbol" and substitute therefor -- symbols--.

Signed and Sealed this

Twenty-sixth Day of April, 1994

*Attest:*

BRUCE LEHMAN

*Attesting Officer*     *Commissioner of Patents and Trademarks*